United States Patent [19]
Visveshwara

[11] Patent Number: 5,433,205
[45] Date of Patent: Jul. 18, 1995

[54] METHOD OF OPTIMIZING VENTILATION PERFUSION MATCH

[76] Inventor: Nadarasa Visveshwara, 2776 W. Wrenwood, Fresno, Calif. 93711

[21] Appl. No.: 224,767

[22] Filed: Apr. 8, 1994

[51] Int. Cl.$^6$ .............................................. A61B 8/12
[52] U.S. Cl. ............................ 128/661.09; 128/662.06
[58] Field of Search .................. 128/661.08, 661.09, 128/661.1, 662.01, 662.06, 671, 716, 725, 637; 364/413.03, 413.04, 413.07

[56] References Cited

U.S. PATENT DOCUMENTS

| | | |
|---|---|---|
| 4,637,401 | 1/1987 | Johnston . |
| 4,733,669 | 3/1988 | Segal . |
| 4,796,634 | 1/1989 | Huntsman et al. . |
| 4,802,490 | 2/1989 | Johnston . |
| 4,869,263 | 9/1989 | Segal et al. . |
| 4,915,103 | 4/1990 | Visveshwara et al. . |
| 5,038,789 | 8/1991 | Frazin . |
| 5,339,816 | 8/1994 | Akamatsu et al. ............. 128/662.06 |

OTHER PUBLICATIONS

*Model MDV-20 Velocimeter Instruction Manual*; Millar Instruments, Inc.; 1989; p. 2.
Vincent, Jean Louis; "How stable is a 'stable' cardiac output?"; *Critical Care Medicine*; vol. 22, No. 2; Feb., 1994; pp. 188–189.
Sasse, Scott A., et al.; "Variability of cardiac output over time in medical intensive care unit patients"; *Critical Care Medicine*; vol. 22, No. 2; Feb., 1994; pp. 225–232.
"Ventilation–perfusion Abnormalities"; *Concepts in Respiratory Pathophysiology*; undated; pp. 87–93.

*Primary Examiner*—George Manuel
*Attorney, Agent, or Firm*—Majestic, Parsons, Siebert & Hsue

[57] ABSTRACT

A method of using a Doppler-tipped catheter to produce an indication of the blood flow through an artery can be used for determining shunt fractions through the ductus arteriosus of a neonatal patient. Alternately, this information can be used in the optimizing of a ventilation perfusion match for the patient. Also disclosed is a method of producing a continuous real-time display of the blood flow in an artery with the use of a computer program which can continually produce an indication of the blood flow through an artery.

22 Claims, 8 Drawing Sheets

METHOD OF OPTIMIZING VENTILATION PERFUSION MATCH

A microfiche appendix of a computer program listing for this application consists of one microfiche having 33 frames

BACKGROUND OF THE INVENTION

The present invention concerns a method for optimizing the ventilation perfusion match.

The lungs obtain oxygen from the atmosphere and eliminate carbon dioxide produced by the metabolism of the body. This exchange occurs in the alveoli, which are the terminal sacs of the respiratory system. These sacs are fine in thickness and are covered by blood from the pulmonary artery on the outside. Carbon dioxide from the blood diffuses out through the cell layers of the alveoli into the alveoli and then is exhaled from the lung to the outside atmosphere. Similarly, oxygen diffuses the other way—from the lung into the blood. For this reason, any factor affecting the influx and efflux of gases into the lung (V) or affecting the amount of blood available for exchange of gases (Q), will impact the amount of oxygen reaching the body or carbon dioxide being eliminated. The ventilation perfusion match is described in the textbook "Scarpellis Book on Neonatal Respiratory Physiology," p. 87–93, which is incorporated herein by reference.

It is desired to have an improved method of determining and adjusting the ventilation perfusion match.

SUMMARY OF THE INVENTION

The present invention involves placing a Doppler-tipped catheter into an artery of the patient. Placing the Doppler-tipped catheter into an artery allows for a greater control of the angle of the beam coming from the tip of the Doppler-tipped catheter than in other methods. Although the method of the present invention is invasive, in some situations a catheter needs to be placed in the artery for some other reason. A catheter may be placed into the artery of a premature baby or in the artery of an adult who is undergoing heart surgery.

A Doppler-tipped catheter placed in an artery is used in the methods of the present invention. One method of the present invention involves a method of optimizing the ventilation perfusion match in a patient. This method involves artificially ventilating the patient; catheterizing a Doppler-tipped catheter into an artery of the patient, the catheter being aligned along the length of the artery; emitting a signal from the Doppler-tipped catheter; measuring a frequency-shift signal of the signal reflected back to the tip of the catheter, the frequency-shift signal being proportional to the blood flow velocity in the artery; and using information from the frequency-shift signal to aid in the optimization of the ventilation perfusion match.

An additional method of the present invention involves producing a real-time continuous display of the blood flow through an artery, rather than producing an intermittent indication of the blood flow in an artery. A recent article, Sasse et al., "Variability of cardiac output over time in medical intensive care unit patients," Critical Care Medicine, Volume 22, No. 2, pp. 225–232, suggests that variations in cardiac output may be relatively large due to changes in physiologic indices and the ventilator effect. For that reason, a real time continuous display of blood flow may have benefits over intermittent indications. Additionally, the real-time display can be useful, for example, in the ventilation perfusion match. This method involves obtaining a real-time display of a cardiac output of a patient, including the steps of catheterizing the Doppler-tipped catheter into an artery of the patient, the catheter being aligned along the length of the artery; emitting a signal from the Doppler-tipped catheter; measuring a frequency-shift signal of the signal reflected back to the tip of the catheter, the frequency-shift signal being proportional to the blood flow velocity in the artery; and producing from said frequency-shift signal a real-time display of the blood flow through the artery.

Additionally, the present invention includes a method for determining shunt fractions through the ductus arteriosus. The ductus arteriosus is a passageway between the aorta and the pulmonary artery which allows blood from the umbilical cord of a fetus to pass through to the body of the fetus. The ductus arteriosus begins to contract immediately after respiration is established, and normally becomes completely closed from the fourth to the tenth day. Shunt fractions through the ductus arteriosus can make measurement of blood flow, and ultimately the optimization of the ventilation perfusion match, difficult for neonatal patients.

The present invention involves a method of determining shunt fractions through the ductus arteriosus in a neonatal patient, the method comprising the steps of catheterizing the Doppler-tipped catheter into an artery of the patient, the catheter being aligned along the length of the artery such that the tip of the catheter is near the ductus arteriosus; and measuring a frequency-shift signal of the signal reflected back to the tip of the catheter, the frequency-shift signal being proportional to the blood flow velocity wherein the Doppler-tipped catheter is aligned in the catheterizing step such that the frequency-shift signal enables the shunt fraction through the ductus arteriosus to be determined.

BRIEF DESCRIPTION OF THE DRAWINGS

The above and other features and aspects of the present invention will become more apparent upon reading the following detailed description in conjunction with the accompanying drawings, in which.

DETAILED DESCRIPTION OF THE PREFERRED EMBODIMENT

Figure 1:
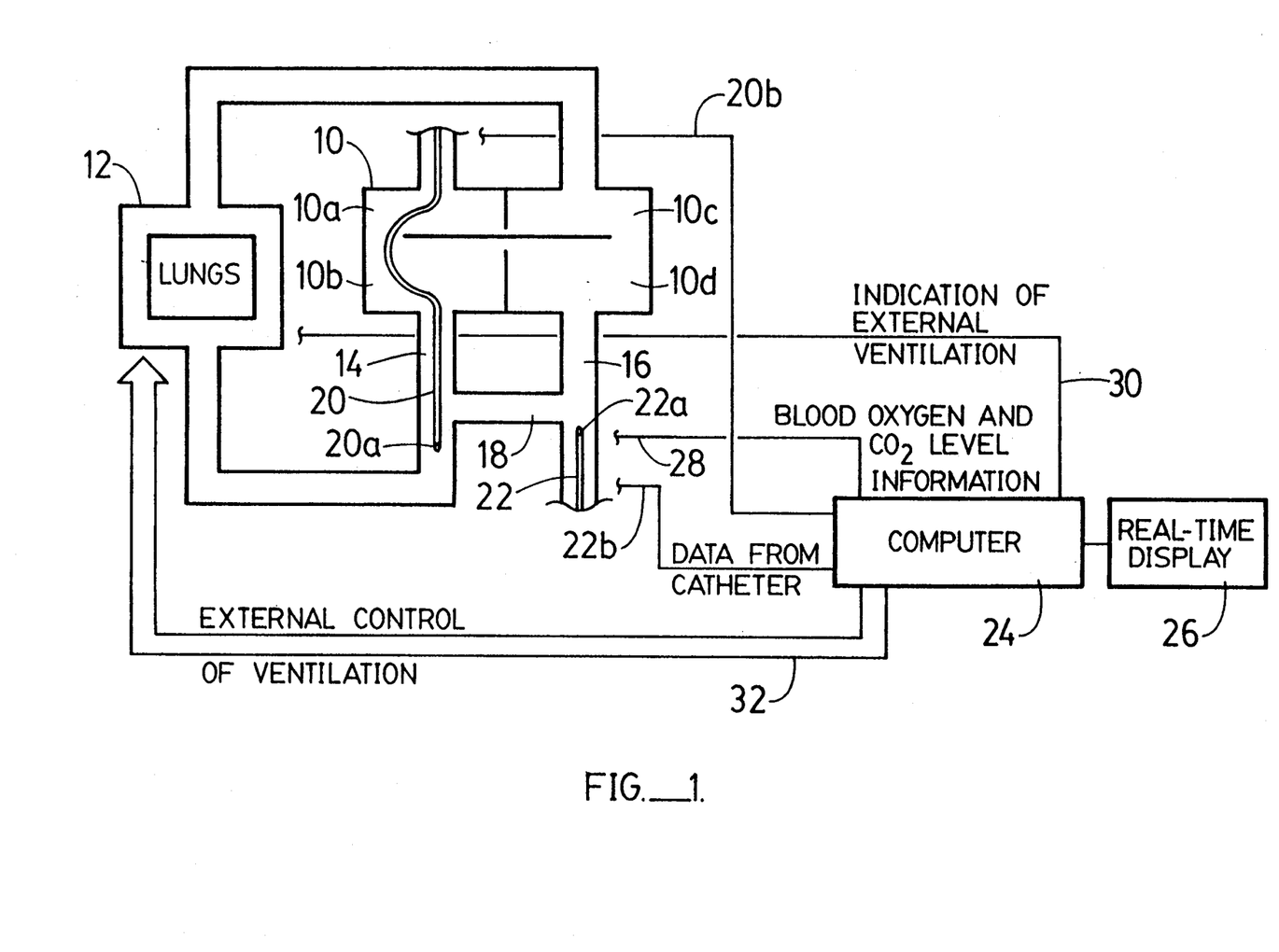
FIG. 1 is a schematic view of parts of the human body, including the heart and lung. This schematic also shows the positions of Doppler-tipped catheters and shows a computer, which can be used for determining the blood flow in a portion of the body.

FIG. 1 is a schematic view of parts of the body, including the heart 10 and lungs 12. The heart is divided into the right atrium 10a and right ventricle 10b, and the left atrium 10c and left ventricle 10d. The pulmonary artery 14 connects the right ventricle 10b to the lungs 12. The aorta 16 is a passage through which blood goes to the different parts of the body. In a fetus and neonatal patient, the pulmonary artery 14 and aorta 16 are connected by the ductus arteriosus 18.

FIG. 1 shows two positions in which a catheter can be placed into the arteries to determine the blood flow of the patient. Doppler-tipped catheter 20 is positioned down through the heart past the ductus arteriosus in the pulmonary artery 14. Notice that the tip of the Doppler-tipped catheter 20a is near but facing away from the ductus arteriosus 18. Doppler-tipped catheter 22 is placed through the umbilical cord up through the aorta 16 to a position near and facing the ductus arteriosus 18. The velocity of blood in the bloodstream can be determined with the use of a Doppler-tipped catheter in a manner such that the cardiac output can be computed with the equation $Q=AZ$, where Q is the blood flow, A is the cross-sectional area of the blood vessel, and Z is the mean velocity of the blood through the vessel. The mean velocity Z is determined using the Doppler shift in the frequency between the transmitted signal and the received signal. This shift $\Delta f$ is proportional to the blood velocity. This is expressed by the equation $\Delta f = (2fV \cos\theta)/C$, where V is the mean velocity, f is the frequency of the incident sound, C is the velocity of sound in tissue, and $\theta$ is the angle of incidence of the sound beam from the Doppler-tipped catheter. If the transmitting frequency, velocity of sound in tissue, and angle of incidence is kept constant, the frequency shift is proportional to the blood flow velocity.

An important part of monitoring the ventilation perfusion match is monitoring the blood flow in the body. When patients are on life support systems, oxygen is pumped under pressure into the lung 12 at high concentrations. Thus, if the surface area of the lung 12 available for gas exchange is decreased by disease, e.g. pneumonia, the higher concentration of oxygen will provide an adequate amount of oxygen to the body through the available surface area. Sometimes the lung 12 tends to collapse or have poor compliance, as in premature infants. Pressure to deliver the oxygen and open the lungs then becomes essential. However, excess pressure will over-distend the alveoli and squeeze the surrounding blood out, causing an inadequate availability of blood for gas exchange. In this case, due to over-distension, V is increased; however, due to the squeeze effect, Q is decreased. Catheter 20a will show decreased flow. Conversely, if the pressure is inadequate, the blood supply remains adequate but the gas supply is reduced—normal Q with decreased V. Please note that the concentration of oxygen may be adequate, just that the surface area available for gas exchange is reduced. In the last case, catheter 20a will show normal flow.

Right to left shunting is used loosely with any condition that leads to inadequate oxygenation of the body. Left to right shunting refers to excess blood supply to the lung.

The ductus arteriosus 18 complicates the above picture. If this conduit between the pulmonary artery, the main blood vessel to the lung, and the aorta, the main blood vessel in the body, does not close, the blood takes the path of least resistance and may bypass the lung completely. This effect is caused by excess pressure or over-distension of the lung described above—right to left shunting with $V/Q>1$. On the other hand, normally the pressure in the aorta is higher than that of the pulmonary artery. Hence, if the ductus is open, the blood will leak back into the lungs—left to right shunting with $V/Q<1$. Catheter 22a will show retrograde flow and catheter 20a will show increased antegrade flow. This assumes that normal $V/Q=1$.

Placing the catheters within the arteries has advantages over the method of determining the blood flow in the body as described in Huntsman, et al. U.S. Pat. No. 4,796,634. This patent describes a non-invasive method of determining the blood flow in portions of the body. A probe is placed in the esophagus near a portion of the artery. The probe is positioned with ultrasound. Signals from the probe pass through the esophagus into the aorta and reflect off the blood flowing through the artery back to the probe. The probe can then determine the frequency shift of the reflected signal compared to the incident signal. This frequency shift enables a determination of the blood flow through the artery. Since the probe is not placed in the artery, the angle of incidence of the probe beam to the blood flow may be as much as fifteen degrees out of position. This misalignment can result in an inaccurate blood flow calculation. Additionally, if the patient is an infant on a respirator, there can be significant movement of the vasculature during ventilator cycling. This movement may affect the accuracy of the blood flow determination.

In a preferred embodiment of the present invention, the Doppler-tipped catheter is of a type commercially available, having a size of 3.5 to 5.0 Fr. The catheter is preferably 3.0 Fr. in size. The Doppler-tipped catheter has a doughnut-shaped crystal at its tip, which produces a 20 MHz incident sound beam frequency. The length of the Doppler-tipped catheter can be shortened to a size suitable for use in the umbilical cord, if it is to be placed into the aorta 16. In a preferred embodiment, the catheter is the Millar MIKRO-TIP® Doppler Catheter Model DC-201 available from Millar Instruments Inc., located in Houston, Tex. A velocimeter (not shown) such as the 20 MHz pulsed Doppler velocimeter, Model MDV-20, available from Millar Instruments, is attached to the catheter to produce a blood flow velocity signal.

Figure 2:
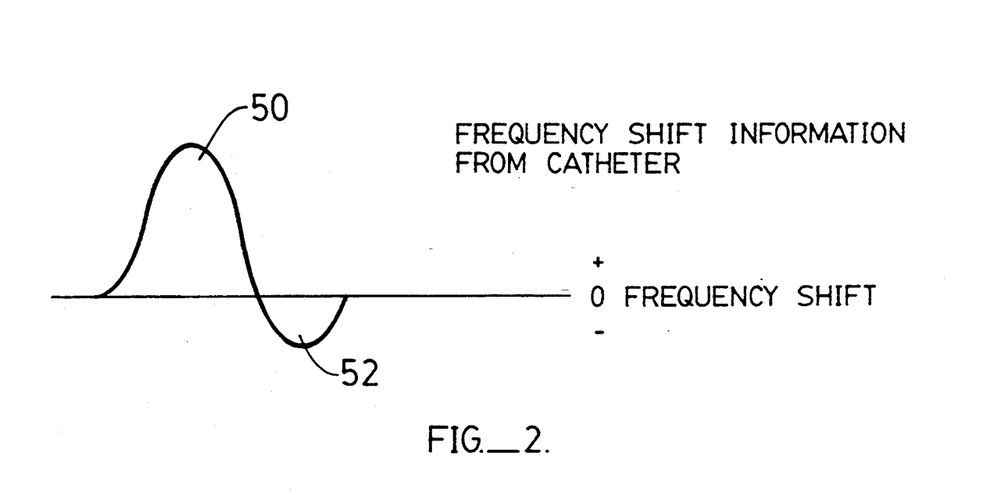
FIG. 2 is a graph of a frequency-shift signal showing antegrade and retrograde portions.

The Doppler-tipped catheter placed into an artery of the patient can help determine shunt fractions through the ductus arteriosus 18. FIG. 2 is a graph showing the frequency shift signal from the Doppler-tipped catheter 22. The antegrade portion 50 gives an indication of the blood flow through the aorta 16 to the body. The retrograde portion 52 gives an indication of the left-to-right shunting of blood flow through the ductus arteriosus 18. In this manner, the shunt fraction through the ductus arteriosus 18 can be determined. Alternately, a Doppler-tipped catheter 20 of FIG. 1 will have a retrograde portion of a frequency shift data which corresponds to the blood flow from the right ventricle 10d to the lungs 12, with an antegrade portion which shows the right-to-left shunting through the ductus arteriosus 18. The signal from the velocimeter connected to the catheter can be set to measure blood flow velocity toward (antegrade) or away from (retrograde) the catheter. The software in the computer 24 switches the velocimeter so as to alternately analyze the antegrade and retrograde portion of the signal every 50 milliseconds.

The catheter 20a placed in the pulmonary artery 14 can reveal the nature and characteristics of pulsatile flow in the pulmonary artery. The pressure in the pulmonary artery due to the pumping of the heart varies with time. There is a pressure gradient between the systolic and diastolic pressure that can be indirectly determined with the change of blood flow velocity measured with catheter 20a. Further, the effects of vasoactive medication or muscle relaxants on the pulmonary artery can be studied by use of the catheter 20a.

Looking again at FIG. 1, the frequency shift data from the Doppler-tipped catheter 20 can be sent along line 20b to computer 24. The frequency shift data from Doppler-tipped catheter 22 can be sent along line 22b to the computer 24. The computer 24 can use the different portions of the frequency shift data to determine the shunt fraction through the ductus arteriosus 18.

Additionally, the frequency shift signal can be integrated in the computer 24 and then multiplied by a factor which corresponds to the cross-sectional area of the artery in which a catheter is placed in order to determine the blood flow through the artery in which the catheter is placed. The computer software can also be used to quantify any physiological parameter with a phasic output. Examples of physiological parameters with phasic outputs include cardiac output from blood pressure waveform and tidal volume from impedance or flow wave form. The program can synthesize simultaneous data input from surface or indwelling oxygen and carbon dioxide sensors, respiratory volume and flow sensors etc. Thus, their cumulative and individual response to cardiac output and ventilator effect can be determined. In this way, the program can act as an integrated system to determine optimal V/Q match.

In this manner, the computer 24 can in real time produce an indication of the blood flow in an artery. The continuous real-time display 26 can be used by an operator in setting the ventilation perfusion match. Additionally, the computer 24 can receive additional information, such as the blood oxygen and carbon dioxide level on line 28 from a probe (not shown), and an indication of the external ventilation on line 30. In newborns, noninvasive, real-time oxygen and carbon dioxide levels may be obtained. This information aids in the optimization of the ventilation perfusion match.

The computer program presently used in computer 24 with the method of the present invention is a user-friendly program which, among other functions, does the following: displays in real-time the graph of the variation in the velocimeter voltage output (which is an indication of blood flow velocity) versus time, and displays digitally the instantaneous value of the velocimeter voltage output; periodically calculates average values of the antegrade, retrograde and net flows and displays them in a digital format; allows for the capture of data (velocimeter output voltage and time sequence) and its storage in binary/compressed files; reviews the capture of data with displays in the form of graphs showing the variation of the velocimeter output voltage versus time; performs calculations on both live and captured data and the storage of modified data in binary/compressed files (these calculations may include "noise" filtering); and prints graphs of captured data stored in binary files. FIG. 6A–D are flow charts that show the operation of a computer program used with the present invention. Additionally, a microfiche appendix of this computer program is appended to this application.

Looking again at FIG. 1, it is possible that the computer 24 can automatically control the ventilation perfusion match; that is, the computer 24 could use the data input to the computer such as the blood oxygen and carbon dioxide levels and the blood flow levels as well as the indication of the external ventilation on line 30 to determine and execute a step to adjust the ventilation perfusion match. For example, a change could be made to the external control of the ventilation over line 32, or fluids could be added into the blood system or drugs could be used in different areas of the blood system to control the blood pressure in those areas. As described below, these three methods are ways of setting the ventilation perfusion match. The determination of the ventilation over line 30 may be done by the method described in N. Visveshwara et al. U.S. Pat. No. 4,915,103 entitled "Ventilation Synchronizer," which is incorporated herein by reference.

The present method for ventilation perfusion optimization match could also be used for adults, in which the ductus arteriosus 18 is closed. For example, a heart attack may cause dysfunction in the left ventricle 10d. This dysfunction would affect the blood flow in the aorta 16. The calculation of the blood flow with the aid of the Doppler-tipped catheter 22 can aid in the optimizing of the ventilation perfusion match. Since the ductus 18 is closed, the Doppler-tipped catheters 20 and 22 would not need to be located near the ductus arteriosus 18.

The blood flow through the aorta 16 and pulmonary artery 14 or the shunting through the ductus arteriosus 18 gives information that is important for the determining of the ventilation perfusion match. Factors which can change the ventilation perfusion match include increasing the ventilation into the lungs 12. This step increases the amount of oxygen that is placed from blood in the vessels in the lungs 12. Over-ventilation, however, may cause too much pressure in the lungs 12, which would restrict the flow of blood through the pulmonary artery 14. Measuring the blood flow by use of a catheter 20 or 22 can give a more immediate indication of this over-ventilation effect than the blood oxygen level. If the operator or the automated computer system 24 determines that the patient is being overly ventilated, ventilation can be reduced, which may actually increase the amount of oxygen sent to the body through the aorta 16. Additionally, with the indications of blood oxygen level and carbon dioxide level, as well as the external ventilation level, and information from a catheter 20 or 22, the V/Q can be optimized by adjusting the ventilator pressures or flow. For example, additional fluid could be added to the system so as to increase the pressures in different parts of the system and adjust the ventilation perfusion match. The use of drugs can also increase or decrease the blood pressure at different portions of the system so as to ultimately aid in the optimization of the ventilation perfusion match. Furthermore, as discussed above, the carbon dioxide level of the blood needs to be monitored in order to ensure that it does not go below a certain level.

Figure 3:
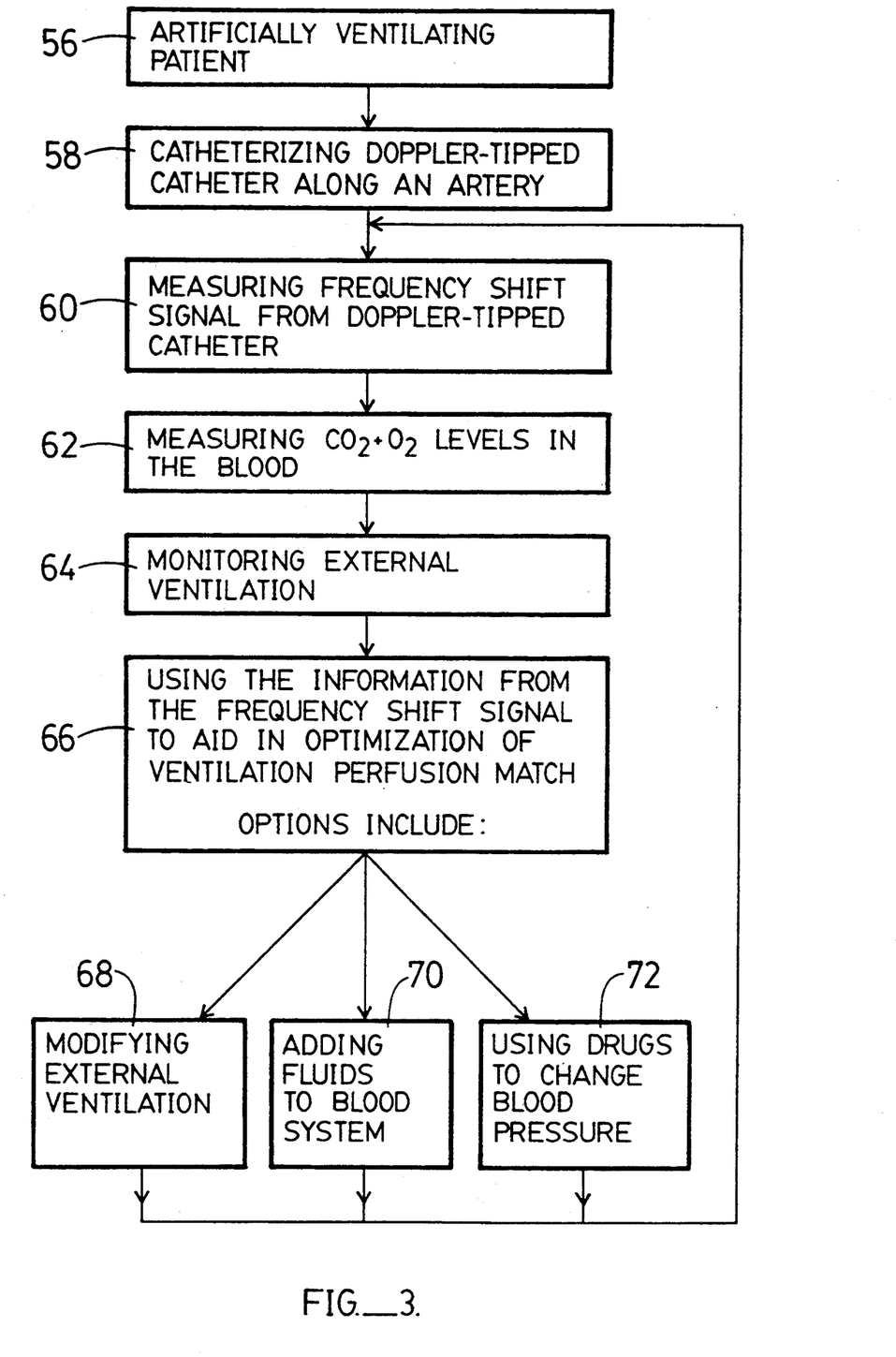
FIG. 3 is a flow chart showing a method of optimizing the ventilation perfusion in a patient.

FIG. 3 is a flow chart showing a method of optimizing the ventilation perfusion match of the present invention. In step 56, the patient is artificially ventilated, as is known in the prior art. Next, a Doppler-tipped catheter is placed along an artery of the patient in step 58. The Doppler-tipped catheter then sends out a signal. Reflections from the red blood cells in the artery produce a frequency-shift signal. This frequency-shift signal is measured by the Doppler-tipped catheter in step 60. A velocimeter produces an indication of blood flow velocity from the frequency shift signal from the catheter. This frequency-shift signal can be analyzed to produce an indication of the blood flow through the arteries.

This could be sent, for example, to a computer such as computer 24 shown in FIG. 1.

Looking again in FIG. 3, in step 62, the carbon dioxide and oxygen levels in the blood are measured and determined. In step 64, the external ventilation to the patient is monitored. In step 66, using the information from the frequency-shift signal, the optimization of the ventilation perfusion match is done. This information could be sent to a computer such as computer 24 shown in FIG. 1, the computer 24 could produce indications of the blood flow, oxygen and carbon dioxide levels, as well as the external ventilation level, so that an operator could determine whether to perform one of the optimization perfusion steps. These optimization steps include step 68, modifying the external ventilation; step 70, adding fluids to the blood system; or step 72, using drugs to change the blood pressure in a portion of the blood system. From each of these three steps, the flow chart loops back up to step 60 to show that this ventilation perfusion optimization is a continual process. Eventually, the steps 68 through 72 could be automated by a computer which receives the indications of the data produced in steps 60 through 64.

Figure 4:
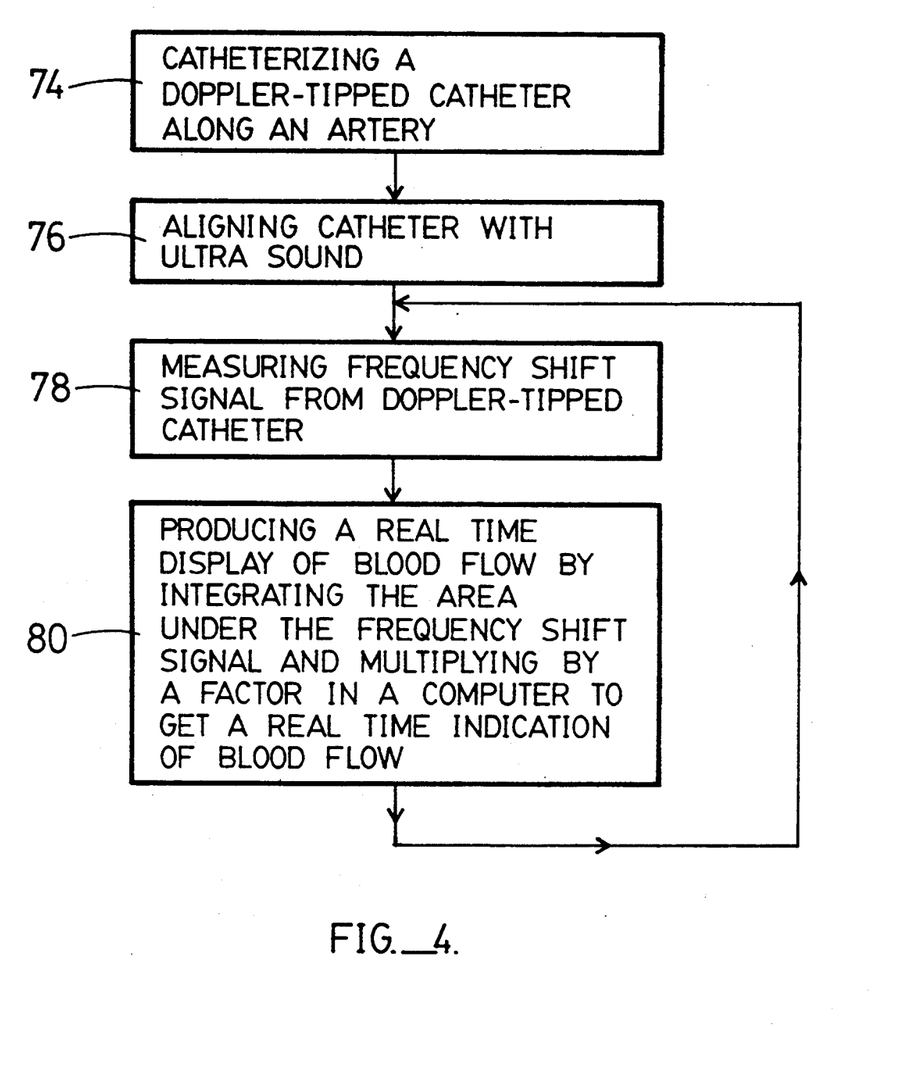
FIG. 4 is a flow chart showing a method of producing a real-time display of blood flow with the use of a Doppler-tipped catheter placed within an artery.

FIG. 4 is a flow chart showing a method for the continual real-time production of blood flow information. This method involves the steps of catheterizing a Doppler-tipped catheter along an artery in step 74, aligning the catheter with ultrasound in step 76, and measuring the frequency shift signal from the Doppler-tipped catheter in step 78. The frequency-shift signal is produced from the returned frequency signal of the Doppler-tipped catheter. A velocimeter connected to the catheter produces an indication of blood flow velocity. A computer system 24 like that shown in FIG. 1 can produce in step 80 a real-time display of the blood flow by integrating the area under the blood flow velocity signal and multiplying by a factor in the computer to get a real-time indication of the blood flow. The factor corresponds to the area of the artery. The method moves back to step 78 to show that this real-time display is a continuous system.

Figure 5:
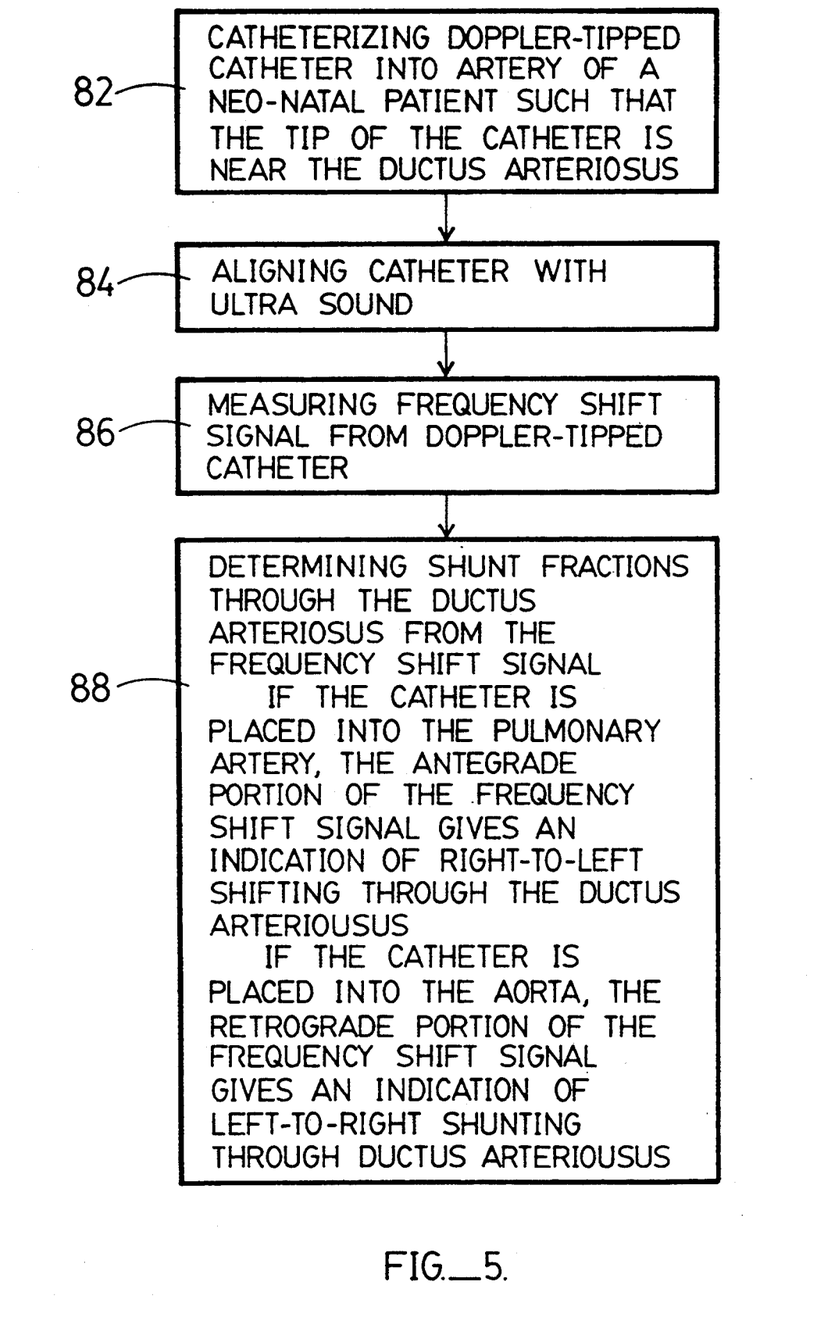
FIG. 5 is a flow chart showing a method of determining shunt fractions in a neonatal patient with the use of a Doppler-tipped catheter placed into an artery of a neonatal patient.
Figure 6A:
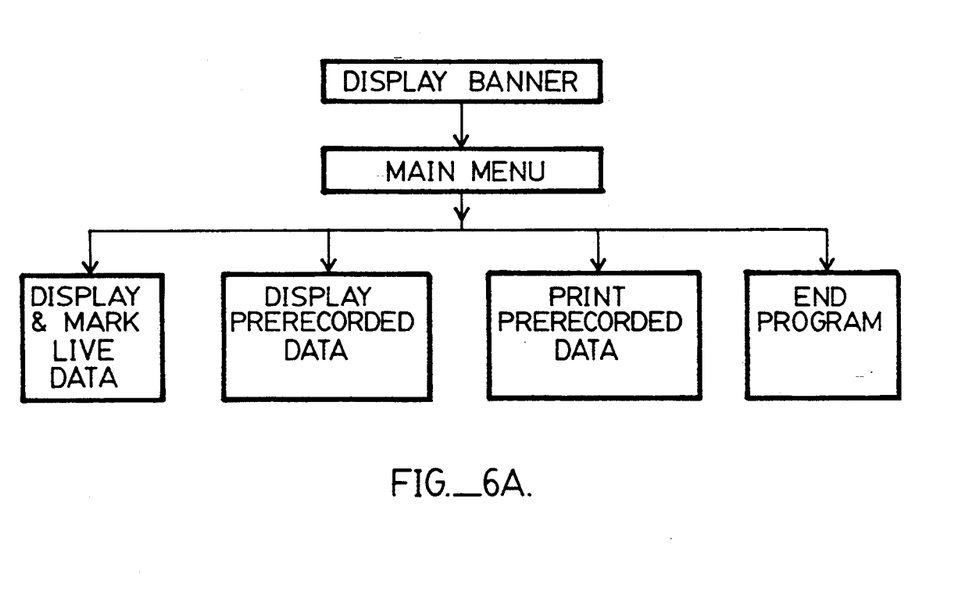
FIGS. 6A–D are flow charts that show the operation of a computer program used with the present invention.
Figure 6B:
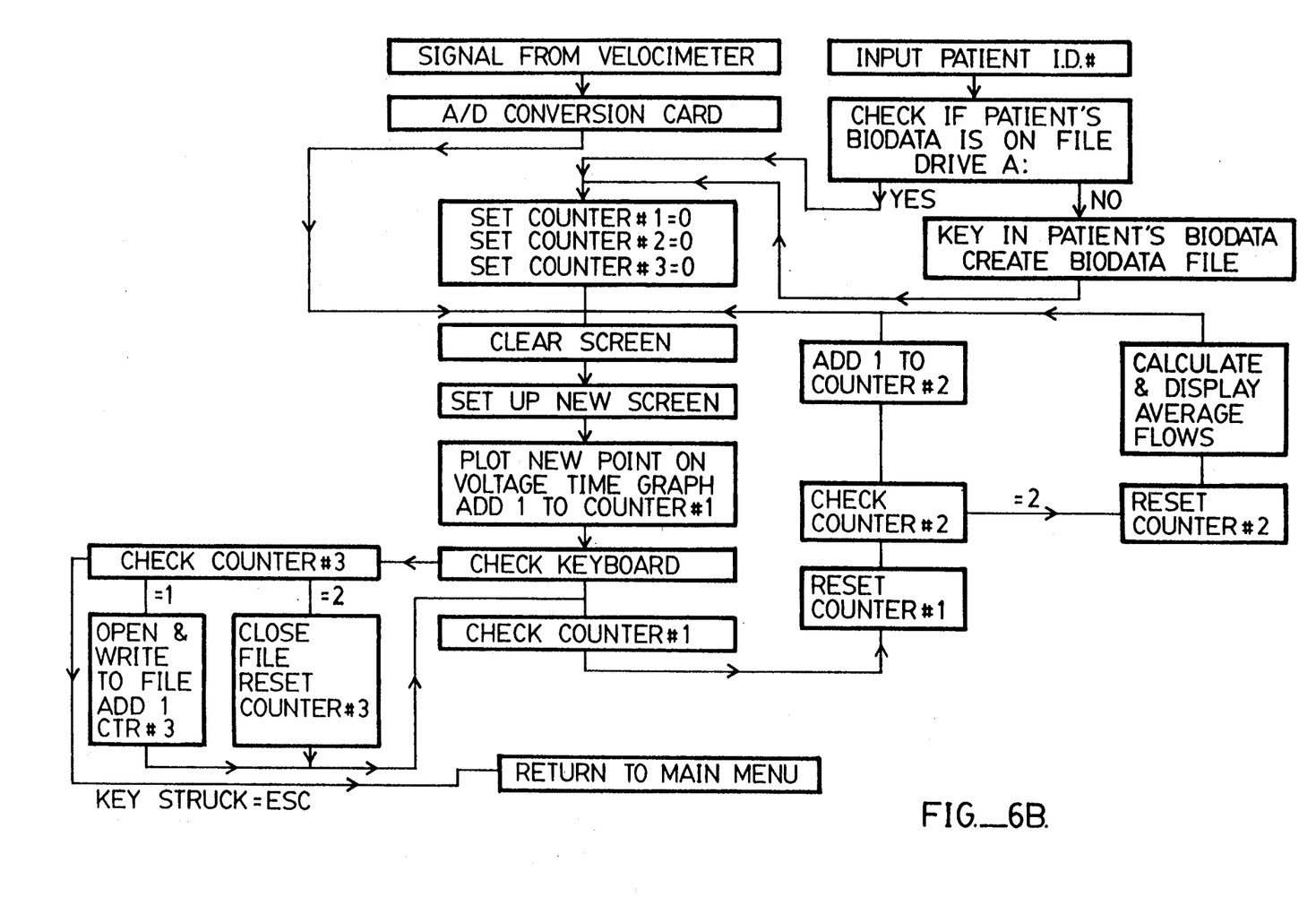
Figure 6C:
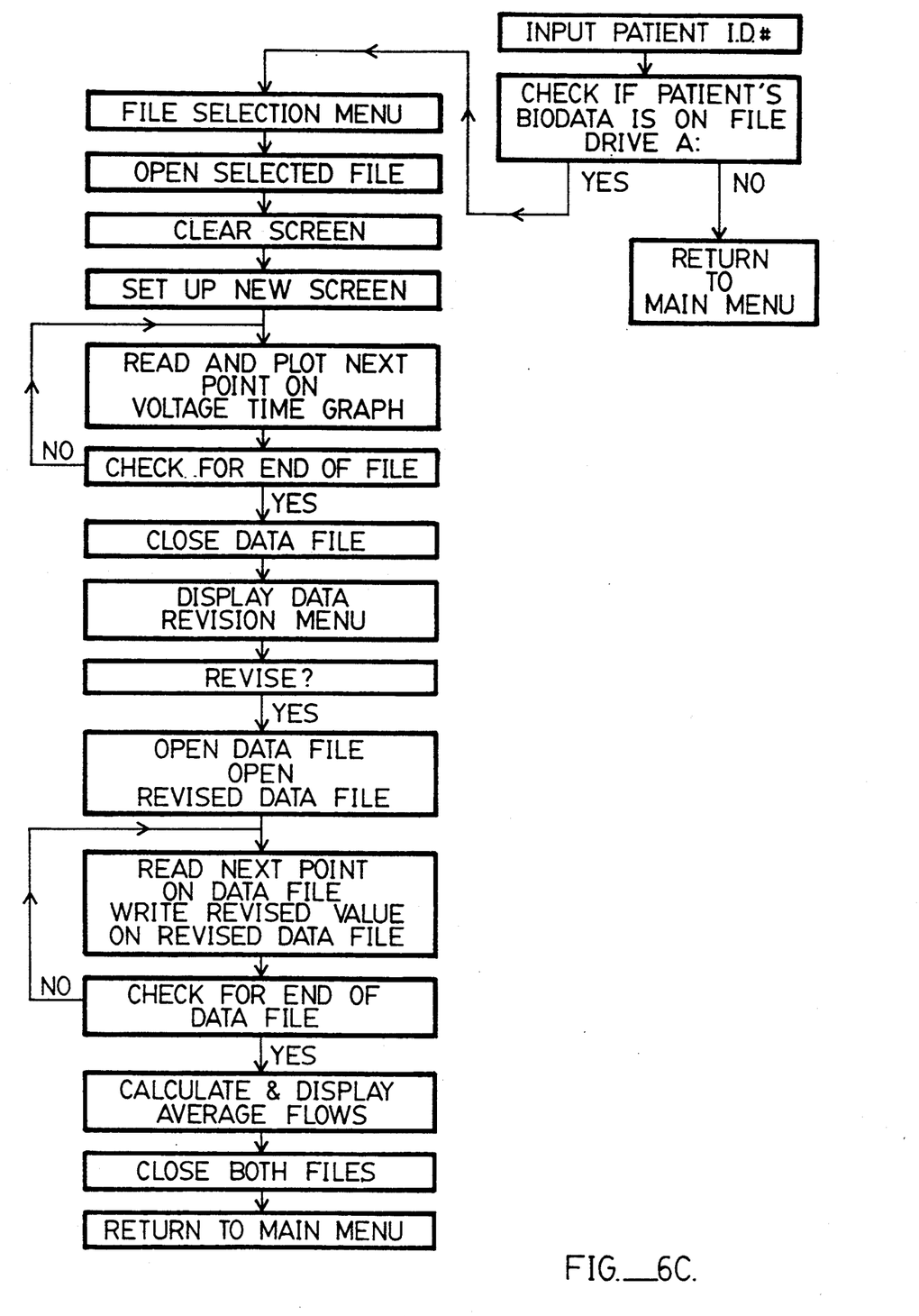
Figure 6D:
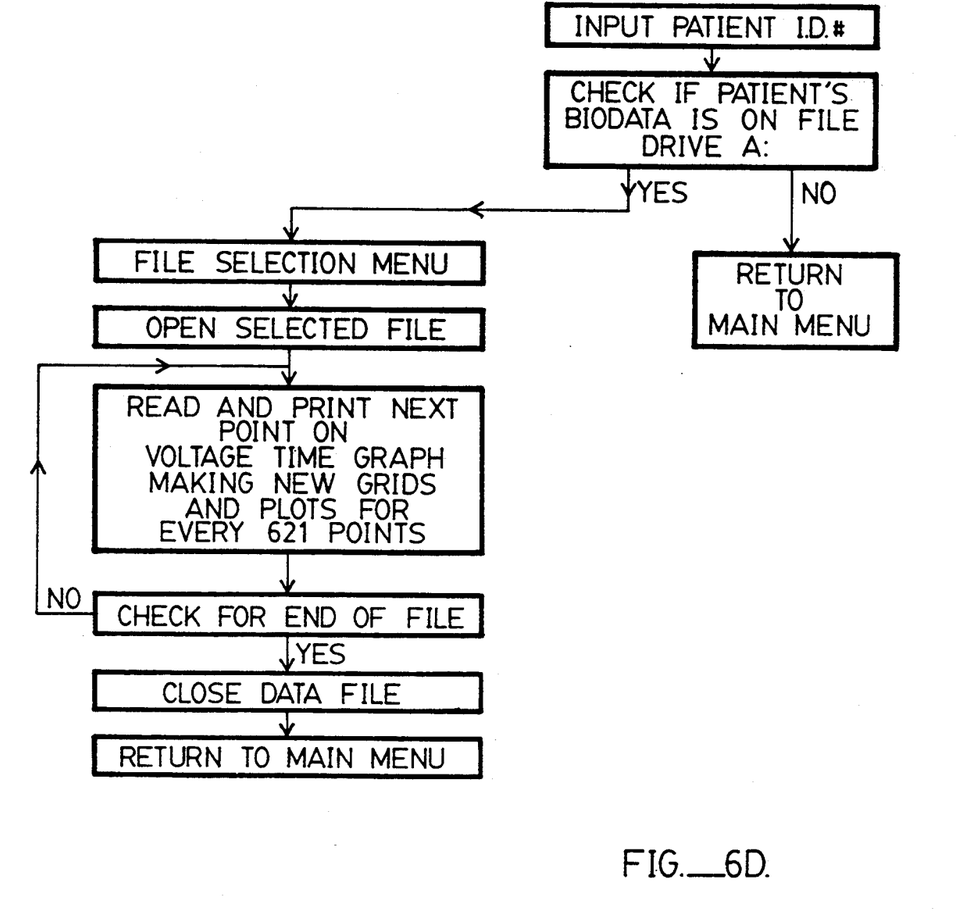

FIG. 5 is a flow chart showing a method of determining the shunt fractions through the ductus arteriosus in a neonatal patient. Step 82 comprises catheterizing the Doppler-tipped catheter into the artery of a neonatal patient such that the tip of the catheter is near the ductus arteriosus. Step 84 involves aligning the catheter with ultrasound. This aligning step can ensure that the tip of the catheter is near the ductus arteriosus. Step 86 involves measuring the frequency-shift signal from the Doppler-tipped catheter. Step 88 involves determining the shunt fractions through the ductus arteriosus by use of the frequency shift signal. As discussed above, if the catheter is placed into the pulmonary artery, the antegrade portion of the frequency-shift signal is an indication of the right-to-left shifting through the ductus arteriosus. If the catheter is placed into the aorta, the retrograde portion of the frequency-shift signal gives an indication of the left-to-right shunting through the ductus arteriosus.

Various details of the implementation and method are merely illustrative of the invention. It will be understood that various changes in the details may be within the scope of the invention, which is to be limited only by the appended claims.

What is claimed:

1. A method of optimizing the ventilation perfusion match in a patient, said method employing a Doppler-tipped catheter, the catheter being generally elongated in shape and having a tip at one end, the tip including a crystal to permit emission of a signal, the catheter being adapted to permit measurement of the signal frequency reflected back to the catheter, said method comprising the steps of:

artificially ventilating the patient by externally supplying positive or negative pressure to the patient's thorax;

catheterizing the Doppler-tipped catheter into an artery of the patient, the catheter being aligned along the length of the artery;

emitting the signal from the Doppler-tipped catheter;

measuring a frequency shift signal of the signal reflected back to the tip of the catheter, the frequency shift signal being proportional to the blood flow velocity in the artery; and using the frequency shift signal to improve the ventilation perfusion match.

2. The method of claim 1, wherein said artificial ventilating step includes the step of generating a signal indicating the level of the ventilation to the patient.

3. The method of claim 1, further comprising the step of generating a signal indicating the patient's blood oxygen level.

4. The method of claim 3 further comprising the step of generating a signal indicating the carbon dioxide level in the patient's blood.

5. The method of claim 1, wherein the frequency shift signal is automatically used by a controller to improve the ventilation perfusion match.

6. The method of claim 1, wherein the patient is a neonatal patient with an open ductus arteriosus, and wherein the catheterizing step is aligned such that the tip of the catheter is near the ductus arteriosus and wherein the frequency shift signal using step includes determining the direction and quantity of the flow of fluid through the ductus arteriosus.

7. The method of claim 1, wherein the patient is an adult patient.

8. The method of claim 1, wherein the frequency shift signal using step includes adding fluid into the patient's body to adjust the ventilation perfusion match.

9. The method of claim 1 wherein the frequency shift signal using step includes changing the blood pressure in part of the patient's body.

10. The method of claim 1 wherein the frequency shift signal using step includes changing the ventilation into the lungs of the patient.

11. A method of obtaining a real-time display of cardiac output in a patient, said method employing a Doppler-tipped catheter, the catheter being generally elongated in shape and having a tip at one end, the tip including a crystal to permit emission of a signal, the catheter being adapted to permit measurement of the signal frequency reflected back to the catheter, said method comprising the steps of:

catheterizing the Doppler-tipped catheter into an artery of the patient, the catheter being aligned along the length of the artery;

emitting the signal from the Doppler-tipped catheter;

measuring a frequency-shift signal of the signal reflected back to the tip of the catheter, the frequency-shift signal being proportional to the blood flow velocity in the artery; and producing from said frequency-shift signal a real-time display of the blood flow through the artery wherein the real-time display producing step includes using a computer to integrate an area under the curve of the frequency-shift signal with respect to time and multiplying the integrated value by a factor to produce an indication of the blood flow through the artery.

12. The method of claim 11, further comprising measuring another physiologic output having phasic changes and producing an integrated indication of this output using the computer.

13. The method of claim 11, wherein the display-producing step includes the step of producing indications of the antegrade and retrograde flow.

14. A method of obtaining a real-time display of cardiac output in a patient, said method employing a Doppler-tipped catheter, the catheter being generally elongated in shape and having a tip at one end, the tip including a crystal to permit emission of a signal, the catheter being adapted to permit measurement of the signal frequency reflected back to the catheter, said method comprising the steps of:
catheterizing the Doppler-tipped catheter in a pulmonary artery of the patient, the catheter being aligned along the length of the pulmonary artery;
emitting the Signal from the Doppler-tipped catheter;
measuring a frequency-shift signal of the signal reflected back to the tip of the catheter, the frequency-shift signal being proportional to the blood flow velocity in the pulmonary artery; and
producing from said frequency-shift signal a real-time display of the blood flow through the pulmonary artery, wherein the real-time display of blood flow gives an indication of the nature and characteristics of the pulsatile flow in the pulmonary artery.

15. The method of claim 14, further comprising the step of supplying vasoactive medication or muscle relaxants to the patient and the step of determining the effects of the vasoactive medicine or muscle relaxants on the pulmonary artery by monitoring the real-time display.

16. A method of determining shunt fractions through the ductus arteriosus in a neonatal patient, said method employing a Doppler-tipped catheter, the catheter being generally elongated in shape and having a tip at one end, the tip including a crystal to permit emission of a signal, the catheter being adapted to permit measurement of the signal frequency reflected back to the catheter, said method comprising the steps of:
catheterizing the Doppler-tipped catheter into an artery of the patient, the catheter being aligned along the length of the artery such that the tip of the catheter is near the ductus arteriosus; and
measuring a frequency-shift signal of the signal reflected back to the tip of the catheter, the frequency-shift signal being proportional to the blood flow velocity wherein the Doppler-tipped catheter is aligned in the catheterizing step such that the frequency-shift signal enables the shunt fractions through the ductus arteriosus to be determined.

17. The method of claim 16, wherein the catheterizing step includes the step of using ultrasound to orient the Doppler-tipped catheter.

18. The method of claim 16, wherein the catheterizing step comprises the step of catheterizing the Doppler-tipped catheter in a pulmonary artery, wherein an antegrade portion of the frequency-shift signal gives an indication of the right-to-left shunting through the ductus arteriosus.

19. The method of claim 18, wherein data from the catheter gives an indication of the nature and characteristics of the pulsatile flow in the pulmonary artery.

20. The method of claim 19, further comprising the step of supplying vasoactive medication or muscle relaxants to the patient and the step of determining the effects of the vasoactive medicine or muscle relaxants on the pulmonary artery using the frequency shift signal from the catheter.

21. The method of claim 16, wherein the catheterizing step comprises the step of catheterizing the Doppler-tipped catheter in the aorta, wherein the retrograde portion of the signal gives an indication of the left-to-right shunting through the ductus arteriosus.

22. The method of claim 21, wherein the Doppler-tipped catheter catheterizing step comprises catheterizing the catheter through the umbilical vessel.

* * * * *